United States Patent [19]

Jolivet et al.

[11] Patent Number: 5,631,131
[45] Date of Patent: *May 20, 1997

[54] CDNA PROBES AND ANTIBODIES FOR HUMAN METHENYLTETRAHYDROFOLATE SYNTHETASE

[75] Inventors: Jacques Jolivet, Mount Royal, Canada; Alain Dayan, Tours, France

[73] Assignee: Université De Montréal, Montreal, Canada

[*] Notice: The term of this patent shall not extend beyond the expiration date of Pat. No. 5,389,516

[21] Appl. No.: 374,983

[22] Filed: Jan. 19, 1995

Related U.S. Application Data

[63] Continuation-in-part of Ser. No. 33,857, Mar. 19, 1993, Pat. No. 5,389,516.

[51] Int. Cl.$^6$ .......................... C12N 15/11; C12N 15/12; C12N 15/52; C12Q 1/68
[52] U.S. Cl. .......................... 435/6; 536/24.1; 536/24.3; 536/24.31; 536/23.2; 935/14; 935/78
[58] Field of Search .......................... 435/6; 536/23.2, 536/24.1, 24.3, 24.31

[56] References Cited

U.S. PATENT DOCUMENTS 5,376,658 12/1994 Spears et al. .......................... 514/274
5,389,516 2/1995 Jolivet et al. .......................... 435/6

OTHER PUBLICATIONS

Ullman, B. et al, Proc. Natl. Acad. Sci. USA, 75:980–983, 1978.
Grem, J.L. et al, Cancer Treat. Rep., 71:1249–64, 1987.
Bertrand, R. et al, Bioch. Biophys. Acta, 911:154–61, 1987.
Mullin, R.J. et al, "Then expanding role of folates and fluoropyrimidines in Cancer Chemotherapy", Plenum, New York, pp. 25–38, 1988.
Stover, P. et al, J. Biol. Chem., 265:14227–14233, 1990.
Stover, P. et al, J. Biol. Chem., 266:1543–1550, 1991.
Bertrand, R. et al, J. Biol. Chem., 264:8843–6, 1989.
Hewick, R.M. et al, J. Biol. Chem., 256:7990–7997, 1981.
Frohman, M.A. et al, Proc. Natl. Acad. Sci. USA, 85:8998, 1988.
Hsu, L.M., et al, J. Bacteriology, 161:1162–1170, 1985.
Hum, D.W. et al, The Journal of Biological Chemistry, 263(13): 15946–15950, 1988.
Thigpen, M. et al, The Journal of Biological Chemistry, 265(14):7907–7913, 1990.
Mascisch, A. et al, Somatic Cell and Molecular Genetics, 17(4):391–398, 1991.
Peri, K.G. et al, FEBS Letters, 294(1–2):113–115, 1991.

*Primary Examiner*—Dian C. Jacobson
*Assistant Examiner*—William W. Moore
*Attorney, Agent, or Firm*—Jacobson, Price, Holman & Stern, PLLC

[57] ABSTRACT

The present invention relates to a cDNA probe for the detection of the mRNA for human methenyltetrahydrofolate synthetase, which comprises the nucleic acid sequence as shown in FIG. 6 or any functional analogs thereof wherein the hybridization of the probe and the mRNA for human methenyltetrahydrofolate synthetase is substantially preserved. The present invention also relates to a polyclonal antibody or an antigen-binding fragment thereof for the detection of the mRNA for human methenyltetrahydrofolate synthetase, wherein said antibody is raised against a protein segment aa$^{100-112}$ H-Phe-Asp-Lys-His-Gly-Asn-Arg-Leu-Gly-Lys-OH of human methenyltetrahydrofolate synthetase.

4 Claims, 8 Drawing Sheets

```
              GC GAC ACT TAT AAA ATA ACT TGC ATC TAC GCT GGG  -91
CCT GCC GCC TCA CCC TGT AAT CCC AGC ACT TTG GGA GGC CGA AGT  -46
GGG TCG ATC ACT TCA GCC CAG CAC TTT GAG ACC AGC CTG GCC AAC  -1
ATG GTG AAA CCC CAT CTC TAT CAG AAA TAC AAA AGA ATT TCC ATC  45
 M   V   K   P   H   L   Y   Q   K   Y   K   R   I   S   I  15
                          ----IV----
TTT CTG ACC ATG CAA GAT GAA ATT GAG ACA GAA GAG ATC ATC AAG  90
 F   L   S   M   Q   D   E   I   E   T   E   E   I   I   K  30
              ----IV---
GAC ATT TTC CAA CGA GCC AAA ATC TGC TTC ATC CCT CGG TAC CGG  135
 D   I   F   Q   R   G   K   I   C   F   I   P   R   Y   R  45

TTC CAG AGC AAT CAC ATG GAT ATG GTG AGA ATA GAA TCA CCA GAG  180
 F   Q   S   N   H   M   D   M   V   R   I   E   S   P   E   60
                                           ---IV---
GAA ATT TCT TTA CTT CCC AAA ACA TCC TGG AAT ATC CCT CAG CCT  225
 E   I   S   L   L   P   K   T   S   W   N   I   P   Q   P  75

GGT GAG GGT GAT GTT CGG GAG GAG GCC TTG TCC ACA GGG GCA CTT  270
 G   E   G   D   V   R   E   E   A   L   S   T   G   G   L   90

GAT CTC ATC TTC ATG CCA GGC CTT GGG TTT GAC AAA CAT GCC AAC  315
 D   L   I   F   M   P   G   L   G   F   D   K   H   G   N   105
                     ----I----
CCA CTG GGG AGG GGC AAG GGC TAC TAT GAT GCC TAT CTG AAG CGC  360
 R   L   G   R   G   K   G   Y   Y   D   A   Y   L   K   R   120
                ------III------
TGT TTG CAG CAT CAG GAA GTG AAG CCC TAC ACC CTG GCG TTG GCT  405
 C   L   Q   H   Q   E   V   K   P   Y   T   L   A   L   A   135

TTC AAA GAA CAG ATT TGC CTC CAG GTC CCA GTG AAT GAA AAC GAC  450
 F   K   E   Q   I   C   L   Q   V   P   V   N   E   N   D   150
                  ---------II---------
ATG AAG GTA GAT GAA GTC CTT TAC GAA GAC TCG TCA ACA GCT TAA  495
 M   K   V   D   E   V   L   Y   E   D   S   S   T   A   Z   164
                 ----IV----
ATC TGG ATT ACT ACA GCC AAA TAA TCA GTG TTT TAT ATG AGA GTA  540
AAG CAA AGT ATG TGT ATT TTT CCC TTG TCA AAA ATT AGT TGA AAT  585
TGT TCA TTA ATG TGA ATA CAG ACT GCA TTT TAA AAT TGT AAT TAT  630
GAA ATA CCT TAT ATA AAA CCA TCT TTA AAA ACC AAT AGA AGT GTG  675
AAT AGT AGA ATA TTA ATT AAA ATG GAG GCT ATC ACC CTG TCA TTT  720
TCA GCT TAA AAA AAA AAA AAA A                                742
```

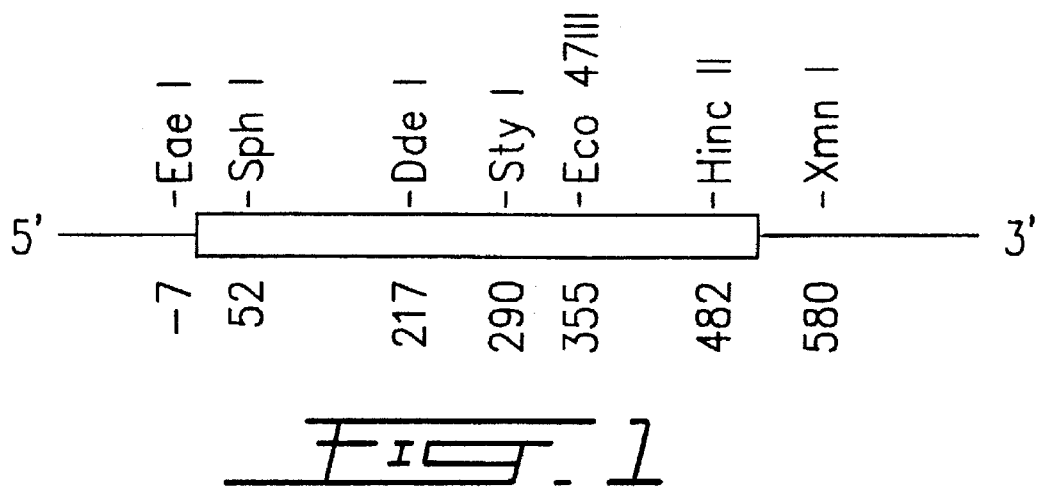

FIG. 1

```
MIRQRRRALTPEQQQEMGQQAATRMMTYPPVVMAHTVAVFLSFDGELDTQ    50 E.Coli
M              VKPHLY    QKYKRISIFLSMQDEIETE          26 Human
-                -         --    - -

PLIEQLWRAGKRVYLPVLHPF SAGNLLFLNYHPQ  SELVMNRLKIHEP    97 E.Coli
EIIKDIFQRGKICFIPRYR  FQSNHMDMVRIESPEEISLLPKTSWNIPQPG  76 Human
 -    --    -  --       - -           - -     -

KLDVR DVLPLSRLDVLITPLVA FDEYGQRLGMGGGFYDRTLQNW QHYH   145 E.Coli
EGDVREEALSTGGLD LIFMPGLGFDKHGNRLGRGKGYYDAYLKRCLQHQE   126 Human
  ---   -  -- --       -  --    - --- --      --

YKTQPVGYAHDCQLVEKLPVEEWDIPLPAVVTP SKVWEW             184 E.Coli
VKPYTLALAFKEQICLQVPVNENDMKVDEVLYEDSSTA               164 Human
 -   -     --- -         - -  -
```

FIG. 3

```
                    GC GAC ACT TAT AAA ATA ACT TGC ATC TAG GCT GGG  -91
CGT GGC GGC TCA CGC TGT AAT CCC AGC ACT TTG GGA GGC CGA AGT        -46
GGG TGG ATC ACT TGA GGC CAG GAG TTT GAG ACC AGC CTG GCC AAC         -1
ATG GTG AAA CCC CAT CTC TAT CAG AAA TAC AAA AGA ATT CCC ATC         45
 M   V   K   P   H   L   Y   Q   K   Y   K   R   I   S   I         15
                                                ----IV----
TTT CTG AGC ATG CAA GAT GAA ATT GAG ACA GAA GAG ATC ATC AAG         90
 F   L   S   M   Q   D   E   I   E   T   E   E   I   I   K         30
        ----IV----
GAC ATT TTC CAA CGA GGC AAA ATC TGC TTC ATC CCT CGG TAC CGG        135
 D   I   F   Q   R   G   K   I   C   F   I   P   R   Y   R         45

TTC CAG AGC AAT CAC ATG GAT ATG GTG AGA ATA GAA TCA CCA GAG        180
 F   Q   S   N   H   M   D   M   V   R   I   E   S   P   E         60
                                            ---IV----
GAA ATT TCT TTA CTT CCC AAA ACA TCC TGG AAT ATC CCT CAG CCT        225
 E   I   S   L   L   P   K   T   S   W   N   I   P   Q   P         75

GGT GAG GGT GAT GTT CGG GAG GAG GCC TTG TCC ACA GGG GGA CTT        270
 G   E   G   D   V   R   E   E   A   L   S   T   G   G   L         90

GAT CTC ATC TTC ATG CCA GGC CTT GGG TTT GAC AAA CAT GGC AAC        315
 D   L   I   F   M   P   G   L   G   F   D   K   H   G   N        105
                 ------------I----------
CGA CTG GGG AGG GGC AAG GGC TAC TAT GAT GCC TAT CTG AAG CGC        360
 R   L   G   R   G   K   G   Y   Y   D   A   Y   L   K   R        120
         ------III------
TGT TTG CAG CAT CAG GAA GTG AAG CCC TAC ACC CTG GCG TTG GCT        405
 C   L   Q   H   Q   E   V   K   P   Y   T   L   A   L   A        135

TTC AAA GAA CAG ATT TGC CTC CAG GTC CCA GTG AAT GAA AAC GAC        450
 F   K   E   Q   I   C   L   Q   V   P   V   N   E   N   D        150
                 ----------------II----------------
ATG AAG GTA GAT GAA GTC CTT TAC GAA GAC TCG TCA ACA GCT TAA        495
 M   K   V   D   E   V   L   Y   E   D   S   S   T   A   Z        164
             ----------IV---------
ATC TGG ATT ACT ACA GCC AAA TAA TCA GTG TTT TAT ATG AGA GTA        540
AAG CAA AGT ATG TGT ATT TTT CCC TTG TCA AAA ATT AGT TGA AAT        585
TGT TCA TTA ATG TGA ATA CAG ACT GCA TTT TAA AAT TGT AAT TAT        630
GAA ATA CCT TAT ATA AAA CCA TCT TTA AAA ACC AAT AGA AGT GTG        675
AAT AGT AGA ATA TTA ATT AAA ATG GAG GCT ATC AGC CTG TGA TTT        720
TCA GCT TAA AAA AAA AAA AAA A                                     742
```

```
MTHFS- 5    CGGTGGGAGC CAAGATACAG AGGTAAAATA AAGCATACTC TAGGAAAAGC    50
MTHFS-1     ---------- ---------- ---------- ---------- ----------
MTHFS-2     ---------- ---------- ---------- ---------- ----------
MTHFS-4     ---------- ---------- ---------- ---------- ----------
MTHFS-3     ---------- ---------- ---------- ---------- ----------

MTHFS- 5    ATGTGAAATG ACCGAAGACT ACTAAAATGG ATAGGTGGGG ATCAAGCCTG   100
MTHFS-1     ---------- ---------- ---------- ---------- ----------
MTHFS-2     ---------- ---------- ---------- ---------- ----------
MTHFS-4     ---------- ---------- ---------- ---------- ----------
MTHFS-3     ---------- ---------- ---------- ---------- ----------

MTHFS- 5    GAATTCTCTG GATAGACAGC TTGTCTCCAC AGTGACCTTT TAATGAGTTT   150
MTHFS-1     ---------- ---------- ---------- ---------- ----------
MTHFS-2     ---------- ---------- ---------- ---------- ----------
MTHFS-4     ---------- ---------- ---------- ---------- ----------
MTHFS-3     ---------- ---------- ---------- ---------- ----------

MTHFS- 5    TCACACCTAC CAGAGTGGGT GTACCAGGAA GGGATAAAAG GAGCAGGTAA   200
MTHFS-1     ---------- ---------- ---------- ---------- ----------
MTHFS-2     ---------- ---------- ---------- ---------- ----------
MTHFS-4     ---------- ---------- ---------- ---------- ----------
MTHFS-3     ---------- ---------- ---------- ---------- ----------

MTHFS- 5    GTGCTGGGTC CCAAACTAAA AGTCAGGCTT CATGATGCAA CACTGTCTGA   250
MTHFS-1     ---------- ---------- ---------- ---------- ----------
MTHFS-2     ---------- ---------- ---------- ---------- ----------
MTHFS-4     ---------- ---------- ---------- ---------- ----------
MTHFS-3     ---------- --------GT GAGCAGCGCC AAGCGGAGCT GCGGGGAGAG    32

MTHFS- 5    CCCACTATAT CACTCTGGTC CCCCCCCTTT TTTTTTCTTT TAAATATTTA   300
MTHFS-1     ---------- ------GCGT GGGCGTGAGA TGGCGGCGGC AGCGGTGAGC    34
MTHFS-2     ---------- ---------- ---------- ---------- ----------
MTHFS-4     ---------- --------GC GACACTTATA AAATAACTTG CATCTAGGCT    32
MTHFS-3     CTGAAGCAGC GTCTGCGGGC GATGAGTGCC GAGGAGCGTA CGCCAGTCCC    82

MTHFS- 5    AAGAAATTGG AGAAGGCTGA GAGAGAAGGA GGAATTGTTA AGAGGAGTTG   350
MTHFS-1     AGCGCCAAGC GGAGCCTGCG GGGAGAGCTG AAGCAGCGTC TGCGGCGAT    84
MTHFS-2     ------GGCA CGAGCGAGAG CGAGAGGGCC GCGGGCGGCG GACGCAGCGG    44
MTHFS-4     GGGCGTGGCG GCTCACGCTG TAATCCCAGC ACTTTGGGAG GCCGAAGTGG    82
MTHFS-3     TCGTACTGAG CCAGAAGGTG CGAGGCCGCC CGTAGCGGAA GCCGCGGCGG   132
```

FIG. 6A

```
MTHFS- 5   CTAAATATAG TCTTGGAAAA TATAATTGCC ATAATTTCCC ATTTAGGTGA   400
MTHFS-1    GAGTGCCGAG GAGCGGCTAC GCCAGTCCCG CGTACTGAGC CAGAAGGTGA    134
MTHFS-2    GGCCGGGATG GAGGACGTTA ACTCTAACGT GAACGCGGAC CAGGAGGTGA    94
MTHFS-4    GTGGATCACT TGAGGCCAGG AGTTTGAGAC CAGCCTGGCC AACATGGTGA    132
MTHFS-3    ACAGACCCTC CGAAGCTGGC GGCCAGCGAT TGCTGATCTG TGCATGGTGA    182

MTHFS- 5   TTGCCCACAG TGACTATCAA AAGTTCAAAA GAATTTCCAT CTTTCTGAGC    450
MTHFS-1    TTGCCCACAG TGACTATCAA AAGTTCAAAA GAATTTCCAT CTTTCTGAGC    184
MTHFS-2    TTGCCCACAG TGACTATCAA AAGTTCAAAA GAATTTCCAT CTTTCTGAGC    144
MTHFS-4    -AACCG-CA- TCTGTATCAG AAATTCAAAA GAATTTCCAT CTTTCTGAGC    179
MTHFS-3    TTGCCCACAG TGACTATCAA AAGTTCAAAA GAATTTCCAT CTTTCTGAGC    232

MTHFS- 5   ATGCAAGATG AAATTGAGAC AGAAGAGATC ATCAAGGACA TTTTCCAACG    500
MTHFS-1    ATGCAAGATG AAATTGAGAC AGAAGAGATC ATCAAGGACA TTTTCCAACG    234
MTHFS-2    ATGCAAGATG AAATTGAGAC AGAAGAGATC ATCAAGGACA TTTTCCAACG    194
MTHFS-4    ATGCAAGATG AAATTGAGAC AGAAGAGATC ATCAAGGACA TTTTCCAACG    229
MTHFS-3    ATGCAAGATG AAATTGAGAC AGAAGAGATC ATCAAGGACA TTTTCCAACG    282

MTHFS- 5   AGGCAAAATC TGCTTCATCC CTCGGTACCG GTTCCAGAGC AATCACATGG    550
MTHFS-1    AGGCAAAATC TGCTTCATCC CTCGGTACCG GTTCCAGAGC AATCACATGG    284
MTHFS-2    AGGCAAAATC TGCTTCATCC CTCGGTACCG GTTCCAGAGC AATCACATGG    244
MTHFS-4    AGGCAAAATC TGCTTCATCC CTCGGTACCG GTTCCAGAGC AATCACATGG    279
MTHFS-3    AGGCAAAATC TGCTTCATCC CTCGGTACCG GTTCCAGAGC AATCACATGG    332

MTHFS- 5   ATATGGTGAG AATAGAATCA CCAGAGGAAA TTTCTTTACT TCCCAAAACA    600
MTHFS-1    ATATGGTGAG AATAGAATCA CCAGAGGAAA TTTCTTTACT TCCCAAAACA    334
MTHFS-2    ATATGGTGAG AATAGAATCA CCAGAGGAAA TTTCTTTACT TCCCAAAACA    294
MTHFS-4    ATATGGTGAG AATAGAATCA CCAGAGGAAA TTTCTTTACT TCCCAAAACA    329
MTHFS-3    ATATGGTGAG AATAGAATCA CCAGAGGAAA TTTCTTTACT TCCCAAAACA    382

MTHFS- 5   TCCTGGAATA TCCCTCAGCC TGGTGAGGGT GATGTTCGGG AGGAGGCCTT    650
MTHFS-1    TCCTGGAATA TCCCTCAGCC TGGTGAGGGT GATGTTCGGG AGGAGGCCTT    384
MTHFS-2    TCCTGGAATA TCCCTCAGCC TGGTGAGGGT GATGTTCGGG AGGAGGCCTT    344
MTHFS-4    TCCTGGAATA TCCCTCAGCC TGGTGAGGGT GATGTTCGGG AGGAGGCCTT    379
MTHFS-3    TCCTGGAATA TCCCTCAGCC TGGTGAGGGT GATGTTCGGG AGGAGGCCTT    432

MTHFS- 5   GTCCACAGGT ATAGAAGACA GAACTGAACT TCAAGCCTGA TGGTGCTCTG    700
MTHFS-1    GTCCAC---- ---------- ---------- ---------- ----------    390
MTHFS-2    GTCCAC---- ---------- ---------- ---------- ----------    350
MTHFS-4    GTCCAC---- ---------- ---------- ---------- ----------    385
MTHFS-3    GTCCAC---- ---------- ---------- ---------- ----------    438
```

FIG. 6B

```
MTHFS- 5    GCAACAGAAA GAGGACACGA GGGAGTAAAG TCCAAATTCA CAGTCCACTG    750
MTHFS-1     ---------- ---------- ---------- ---------- ----------    390
MTHFS-2     ---------- ---------- ---------- ---------- ----------    350
MTHFS-4     ---------- ---------- ---------- ---------- ----------    385
MTHFS-3     ---------- ---------- ---------- ---------- ----------    438

MTHFS- 5    TCAATCCCAA GAGGGACAAA TGAGCTGGAC AGGAACAGGG AGGAAAGACA    800
MTHFS-1     ---------- ---------- ---------- ---------- ----------    390
MTHFS-2     ---------- ---------- ---------- ---------- ----------    350
MTHFS-4     ---------- ---------- ---------- ---------- ----------    385
MTHFS-3     ---------- ---------- ---------- ---------- ----------    438

MTHFS- 5    GAGGGGGACT TGATCTCATC TTCATGCCAG GCCTTGGGTT TGACAAACAT    850
MTHFS-1     -AGGGGGACT TGATCTCATC TTCATGCCAG GCCTTGGGTT TGACAAACAT    439
MTHFS-2     -AGGGGGACT TGATCTCATC TTCATGCCAG GCCTTGGGTT TGACAAACAT    399
MTHFS-4     -AGGGGGACT TGATCTCATC TTCATGCCAG GCCTTGGGTT TGACAAACAT    434
MTHFS-3     -AGGGGGACT TGATCTCATC TTCATGCCAG GCCTTGGGTT TGACAAACAT    487

MTHFS- 5    GGCAACCGAC TGGGGAGGGG CAAGGGCTAC TATGATGCCT ATCTGAAGCG    900
MTHFS-1     GGCAACCGAC TGGGGAGGGG CAAGGGCTAC TATGATGCCT ATCTGAAGCG    489
MTHFS-2     GGCAACCGAC TGGGGAGGGG CAAGGGCTAC TATGATGCCT ATCTGAAGCG    449
MTHFS-4     GGCAACCGAC TGGGGAGGGG CAAGGGCTAC TATGATGCCT ATCTGAAGCG    484
MTHFS-3     GGCAACCGAC TGGGGAGGGG CAAGGGCTAC TATGATGCCT ATCTGAAGCG    537

MTHFS- 5    CTGTTTGCAG CATCAGGAAG TGAAGCCCTA CACCCTGGCG TTGGCTTTCA    950
MTHFS-1     CTGTTTGCAG CATCAGGAAG TGAAGCCCTA CACCCTGGCG TTGGCTTTCA    539
MTHFS-2     CTGTTTGCAG CATCAGGAAG TGAAGCCCTA CACCCTGGCG TTGGCTTTCA    499
MTHFS-4     CTGTTTGCAG CATCAGGAAG TGAAGCCCTA CACCCTGGCG TTGGCTTTCA    534
MTHFS-3     CTGTTTGCAG CATCAGGAAG TGAAGCCCTA CACCCTGGCG TTGGCTTTCA    587

MTHFS- 5    AAGAACAGAT TTGCCTCCAG GTCCCAGTGA ATGAAAACGA CATGAAGGTA    1000
MTHFS-1     AAGAACAGAT TTGCCTCCAG GTCCCAGTGA ATGAAAACGA CATGAAGGTA    589
MTHFS-2     AAGAACAGAT TTGCCTCCAG GTCCCAGTGA ATGAAAACGA CATGAAGGTA    549
MTHFS-4     AAGAACAGAT TTGCCTCCAG GTCCCAGTGA ATGAAAACGA CATGAAGGTA    584
MTHFS-3     AAGAACAGAT TTGCCTCCAG GTCCCAGTGA ATGAAAACGA CATGAAGGTA    637

MTHFS- 5    GATGAAGTCC TTTACGAAGA CTCGTCAACA GCTTAAATCT GGATTACTAC    1050
MTHFS-1     GATGAAGTCC TTTACGAAGA CTCGTCAACA GCTTAAATCT GGATTACTAC    639
MTHFS-2     GATGAAGTCC TTTACGAAGA CTCGTCAACA GCTTAAATCT GGATTACTAC    599
MTHFS-4     GATGAAGTCC TTTACGAAGA CTCGTCAACA GCTTAAATCT GGATTACTAC    634
MTHFS-3     GATGAAGTCC TTTACGAAGA CTCGTCAACA GCTTAAATCT GGATTACTAC    687
```

FIG. 6C

```
MTHFS- 5   AGCCAAATAA TCAGTGTTTT ATATGAGAGT AAAGCAAAGT ATGTGTATTT   1100
MTHFS-1    AGCCAAATAA TCAGTGTTTT ATATGAGAGT AAAGCAAAGT ATGTGTATTT    689
MTHFS-2    AGCCAAATAA TCAGTGTTTT ATATGAGAGT AAAGCAAAGT ATGTGTATTT    649
MTHFS-4    AGCCAAATAA TCAGTGTTTT ATATGAGAGT AAAGCAAAGT ATGTGTATTT    684
MTHFS-3    AGCCAAATAA TCAGTGTTTT ATATGAGAGT AAAGCAAAGT ATGTGTATTT    737

MTHFS- 5   TTCCCTTGTC AAAAATTAGT TGAAATTGTT CATTAATGTG AATACAGACT   1150
MTHFS-1    TTCCCTTGTC AAAAATTAGT TGAAATTGTT CATTAATGTG AATACAGACT    739
MTHFS-2    TTCCCTTGTC AAAAATTAGT TGAAATTGTT CATTAATGTG AATACAGACT    699
MTHFS-4    TTCCCTTGTC AAAAATTAGT TGAAATTGTT CATTAATGTG AATACAGACT    734
MTHFS-3    TTCCCTTGTC AAAAATTAGT TGAAATTGTT CATTAATGTG AATACAGACT    787

MTHFS- 5   GCATTTTAAA ATTGTAATTA TGAAATACCT TATATAAAAC CATCTTTAAA   1200
MTHFS-1    GCATTTTAAA ATTGTAATTA TGAAATACCT TATATAAAAC CATCTTTAAA    789
MTHFS-2    GCATTTTAAA ATTGTAATTA TGAAATACCT TATATAAAAC CATCTTTAAA    749
MTHFS-4    GCATTTTAAA ATTGTAATTA TGAAATACCT TATATAAAAC CATCTTTAAA    784
MTHFS-3    GCATTTTAAA ATTGTAATTA TGAAATACCT TATATAAAAC CATCTTTAAA    837

MTHFS- 5   AACCAATAGA AAAAAAAAA- ---------- ---------- ----------   1219
MTHFS-1    AACCAATAGA AGTGTGAATA GTAGAATATT AATTAAAATG GAGGCTATCA    839
MTHFS-2    AACCAATAGA AGTGTGAATA GTAGAATATT AATTAAAATG GAGGCTATCA    799
MTHFS-4    AACCAATAGA AGTGTGAATA GTAGAATATT AATTAAAATG GAGGCTATCA    834
MTHFS-3    AACCAATAGA AAAAAAAAA- ---------- ---------- ----------    856

MTHFS- 5   ---------- ---------- ---------- ---                      1219
MTHFS-1    GCCTGTGATT TTCAGCTTAA AAAAAAAAAA AAA                       872
MTHFS-2    GCCTGTGATT TTCAGCTTAA AAAAAAAAAA AAA                       832
MTHFS-4    GCCTGTGATT TTCAGCTTAA AAAAAAAAAA AAA                       867
MTHFS-3    ---------- ---------- ---------- ---                       856
```

FIG. 6D

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 479 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:1:

```
GGCCAACATG GTGAAACCCC ATCTCTATCA GAAATACAAA AGAATTTCCA TCTTTCTGAG      60
CATGCAAGAT GAAATTGAGA CAGAAGAGAT CATCAAGGAC ATTTTCCAAC GAGGCAAAAT     120
CTGCTTCATC CCTCGGTACC GGTTCCAGAG CAATCACATG GATATGGTGA AATAGAATC      180
ACCAGAGGAA ATTTCTTTAC TTCCCAAAAC ATCCTGGAAT ATCCCTCAGC CTGGTGAGGG     240
TGATGTTCGG GAGGAGGCCT TGTCCACAGG GGGACTTGAT CTCATCTTCA TGCCAGGCCT     300
TGGGTTTGAC AAACATGGCA ACCGACTGGG GAGGGGCTAC TATGATGCCT ATCTGAAGCG     360
CTGTTTGCAG CATCAGGAAG TGAAGCCCTA CACCTACACC CTGGCGTTGG CTTTCAAAGA     420
ACAGATTTGC CTCCAGGTCC CAGTGAATGA AAACGACATG AAGGTAGATG AAGTCCTTT      479
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Phe Asp Lys His Gly Asn Arg Leu Gly Arg Gly Lys
 1               5                  10
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
CCCTCGAGGT CGACGGTATC GT                                              22
```

( 2 ) INFORMATION FOR SEQ ID NO:4:

( i ) SEQUENCE CHARACTERISTICS:
        ( A ) LENGTH: 6 amino acids
        ( B ) TYPE: amino acid ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

Pro  Gly  Leu  Gly  Phe  Asp
    1                     5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

Gln  Ile  Cys  Leu  Gln  Val  Pro  Val  Asn  Glu
    1                     5                          10

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

Arg  Ala  Cys  Glu
    1

( 2 ) INFORMATION FOR SEQ ID NO:7:

( i ) SEQUENCE CHARACTERISTICS:
        ( A ) LENGTH: 184 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

| Met | Ile | Arg | Gln | Arg | Arg | Arg | Ala | Leu | Thr | Pro | Glu | Gln | Gln | Glu |
| 1 | | | | 5 | | | | | 10 | | | | | 15 |

Met Gly Gln Gln Ala Ala Thr Arg Met Met Thr Tyr Pro Pro Val Val
            20              25                  30

Met Ala His Thr Val Ala Val Phe Leu Ser Phe Asp Gly Glu Leu Asp
        35              40              45

Thr Gln Pro Leu Ile Glu Gln Leu Trp Arg Ala Gly Lys Arg Val Tyr
    50              55              60

Leu Pro Val Leu His Pro Phe Ser Ala Gly Asn Leu Leu Phe Leu Asn
65              70              75              80

Tyr His Pro Gln Ser Glu Leu Val Met Asn Arg Leu Lys Ile His
            85              90              95

Glu Pro Lys Leu Asp Val Arg Asp Val Leu Pro Leu Ser Arg Leu
            100             105             110

Asp Val Leu Ile Thr Pro Leu Val Ala Phe Asp Glu Tyr Gly Gln
            115             120             125

Arg Leu Gly Met Gly Gly Gly Phe Tyr Asp Arg Thr Leu Gln Asn
            130             135             140

Trp Gln His Tyr His Tyr Lys Thr Gln Pro Val Gly Tyr Ala His
            145             150             155

Asp Cys Gln Leu Val Glu Lys Leu Pro Val Glu Glu Trp Asp Ile
            160             165             170

Pro Leu Pro Ala Val Val Thr Pro Ser Lys Val Trp Glu Trp
            175             180

( 2 ) INFORMATION FOR SEQ ID NO:8:

( i ) SEQUENCE CHARACTERISTICS:
( A ) LENGTH: 164 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

Met Val Lys Pro His Leu Tyr Gln Lys Tyr Lys Arg Ile Ser Ile
1               5               10              15

Phe Leu Ser Met Gln Asp Glu Ile Glu Thr Glu Glu Ile Ile Lys
            20              25              30

Asp Ile Phe Gln Arg Gly Lys Ile Cys Phe Ile Pro Arg Tyr Arg
            35              40              45

Phe Gln Ser Asn His Met Asp Met Val Arg Ile Glu Ser Pro Glu
            50              55              60

Glu Ile Ser Leu Leu Pro Lys Thr Ser Trp Asn Ile Pro Gln Pro
            65              70              75

Gly Glu Gly Asp Val Arg Glu Glu Ala Leu Ser Thr Gly Gly Leu
            80              85              90

Asp Leu Ile Phe Met Pro Gly Leu Gly Phe Asp Lys His Gly Asn
            95              100             105

Arg Leu Gly Arg Gly Lys Gly Tyr Tyr Asp Ala Tyr Leu Lys Arg
            110             115             120

Cys Leu Gln His Gln Glu Val Lys Pro Tyr Thr Leu Ala Leu Ala

```
                                125                     130                      135
        Phe Lys Glu Gln Ile Cys Leu Gln Val Pro Val Asn Glu Asn Asp
                                140                     145                      150

Met Lys Val Asp Glu Val Leu Tyr Glu Asp Ser Ser Thr Ala
                                155                     160
```

( 2 ) INFORMATION FOR SEQ ID NO:9:

( i ) SEQUENCE CHARACTERISTICS:
        ( A ) LENGTH: 867 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 126..620

( x i ) SEQUENCE DESCRIPTION: SEQ ID NO:9:

```
GCGACACTTA TAAAATAACT TGCATCTAGG CTGGGCGTGG CGGCTCACGC TGTAATCCCA        60

GCACTTTGGG AGGCCGAAGT GGGTGGATCA CTTGAGGCCA GGAGTTTGAG ACCAGCCTGG       120

CCAAC ATG GTG AAA CCC CAT CTC TAT CAG AAA TAC AAA AGA ATT CC           167
      Met Val Lys Pro His Leu Tyr Gln Lys Tyr Lys Arg Ile Ser
        1               5                   10

ATC TTT CTG AGC ATG CAA GAT GAA ATT GAG ACA GAA GAG ATC ATC AAG        215
Ile Phe Leu Ser Met Gln Asp Glu Ile Glu Thr Glu Glu Ile Ile Lys
 15              20                  25                  30

GAC ATT TTC CAA CGA GGC AAA ATC TGC TTC ATC CCT CGG TAC CGG TTC        263
Asp Ile Phe Gln Arg Gly Lys Ile Cys Phe Ile Pro Arg Tyr Arg Phe
                 35                  40                  45

CAG AGC AAT CAC ATG GAT ATG GTG AGA ATA GAA TCA CCA GAG GAA ATT        311
Gln Ser Asn His Met Asp Met Val Arg Ile Glu Ser Pro Glu Glu Ile
                 50                  55                  60

TCT TTA CTT CCC AAA ACA TCC TGG AAT ATC CCT CAG CCT GGT GAG GGT        359
Ser Leu Leu Pro Lys Thr Ser Trp Asn Ile Pro Gln Pro Gly Glu Gly
             65                  70                  75

GAT GTT CGG GAG GAG GCC TTG TCC ACA GGG GGA CTT GAT CTC ATC TTC        407
Asp Val Arg Glu Glu Ala Leu Ser Thr Gly Gly Leu Asp Leu Ile Phe
         80                  85                  90

ATG CCA GGC CTT GGG TTT GAC AAA CAT GGC AAC CGA CTG GGG AGG GGC        455
Met Pro Gly Leu Gly Phe Asp Lys His Gly Asn Arg Leu Gly Arg Gly
 95                 100                 105                 110

AAG GGC TAC TAT GAT GCC TAT CTG AAG CGC TGT TTG CAG CAT CAG GAA        503
Lys Gly Tyr Tyr Asp Ala Tyr Leu Lys Arg Cys Leu Gln His Gln Glu
                 115                 120                 125

GTG AAG CCC TAC ACC CTG GCG TTG GCT TTC AAA GAA CAG ATT TGC CTC        551
Val Lys Pro Tyr Thr Leu Ala Leu Ala Phe Lys Glu Gln Ile Cys Leu
                 130                 135                 140

CAG GTC CCA GTG AAT GAA AAC GAC ATG AAG GTA GAT GAA GTC CTT TAC        599
Gln Val Pro Val Asn Glu Asn Asp Met Lys Val Asp Glu Val Leu Tyr
             145                 150                 155

GAA GAC TCG TCA ACA GCT TAA ATCTGGATTA CTACAGCCAA ATAATCAGTG            650
Glu Asp Ser Ser Thr Ala *
 160             165

TTTTATATGA GAGTAAAGCA AAGTATGTGT ATTTTTCCCT TGTCAAAAAT TAGTTGAAAT       710

TGTTCATTAA TGTGAATACA GACTGCATTT TAAAATTGTA ATTATGAAAT ACCTTATATA       770
```

| AAACCATCTT | TAAAAACCAA | TAGAAGTGTG | AATAGTAGAA | TATTAATTAA | AATGGAGGCT | 830 |
| ATCAGCCTGT | GATTTTCAGC | TTAAAAAAAA | AAAAAA | | | 867 |

( 2 ) INFORMATION FOR SEQ ID NO:10:

( i ) SEQUENCE CHARACTERISTICS:
        ( A ) LENGTH: 872 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:10:

| GCGTGGGCGT | GAGATGGCGG | CGGCAGCGGT | GAGCAGCGCC | AAGCGGAGCC | TGCGGGGAGA | 60 |
| GCTGAAGCAG | CGTCTGCGGG | CGATGAGTGC | CGAGGAGCGG | CTACGCCAGT | CCCGCGTACT | 120 |
| GACCCAGAAG | GTGATTGCCC | ACAGTGAGTA | TCAAAAGTCC | AAAAGAATTT | CCATCTTTCT | 180 |
| GAGCATGCAA | GATGAAATTG | AGACAGAAGA | GATCATCAAG | GACATTTTCC | AACGAGGCAA | 240 |
| AATCTGCTTC | ATCCCTCGGT | ACCGGTTCCA | GAGCAATCAC | ATGGATATGG | TGAGAATAGA | 300 |
| ATCACCAGAG | GAAATTTCTT | TACTTCCCAA | AACATCCTGG | AATATCCCTC | AGCCTGGTGA | 360 |
| GGGTGATGTT | CGGGAGGAGG | CCTTGTCCAC | AGGGGACTT | GATCTCATCT | TCATGCCAGG | 420 |
| CCTTGGGTTT | GACAAACATG | GCAACCGACT | GGGGAGGGGC | AAGGGCTACT | ATGATGCCTA | 480 |
| TCTGAAGCGC | TGTTTGCAGC | ATCAGGAAGT | GAAGCCCTAC | ACCCTGGCGT | TGGCTTTCAA | 540 |
| AGAACAGATT | TGCCTCCAGG | TCCCAGTGAA | TGAAAACGAC | ATGAAGGTAG | ATGAAGTCCT | 600 |
| TTACGAAGAC | TCGTCAACAG | CTTAAATCTG | GATTACTACA | GCCAAATAAT | CAGTGTTTTA | 660 |
| TATGAGAGTA | AAGCAAAGTA | TGTGTATTTT | TCCCTTGTCA | AAAATTAGTT | GAAATTGTTC | 720 |
| ATTAATGTGA | ATACAGACTG | CATTTTAAAA | TTGTAATTAT | GAAATACCTT | ATATAAAACC | 780 |
| ATCTTTAAAA | ACCAATAGAA | GTGTGAATAG | TAGAATATTA | ATTAAATGG | AGGCTATCAG | 840 |
| CCTGTGATTT | TCAGCTTAAA | AAAAAAAAA | AA | | | 872 |

( 2 ) INFORMATION FOR SEQ ID NO:11:

( i ) SEQUENCE CHARACTERISTICS:
        ( A ) LENGTH: 832 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:11:

| GGCACGAGCG | AGAGCGAGAG | GGCCGCGGGC | GGCGGAGGCA | GCGGGGCCGG | GATGGAGGAC | 60 |
| GTTAACTCTA | ACGTGAACGC | GGACCAGGAG | GTGATTGCCC | ACAGTGAGTA | TCAAAAGTCC | 120 |
| AAAAGAATTT | CCATCTTTCT | GAGCATGCAA | GATGAAATTG | AGACAGAAGA | GATCATCAAG | 180 |
| GACATTTTCC | AACGAGGCAA | AATCTGCTTC | ATCCCTCGGT | ACCGGTTCCA | GAGCAATCAC | 240 |
| ATGGATATGG | TGAGAATAGA | ATCACCAGAG | GAAATTTCTT | TACTTCCCAA | AACATCCTGG | 300 |
| AATATCCCTC | AGCCTGGTGA | GGGTGATGTT | CGGGAGGAGG | CCTTGTCCAC | AGGGGACTT | 360 |

| | | | | | |
|---|---|---|---|---|---|
| GATCTCATCT | TCATGCCAGG | CCTTGGGTTT | GACAAACATG | GCAACCGACT | GGGGAGGGGC | 420 |
| AAGGGCTACT | ATGATGCCTA | TCTGAAGCCC | TGTTTGCAGC | ATCAGGAAGT | GAAGCCCTAC | 480 |
| ACCCTGGCGT | TGGCTTTCAA | AGAACAGATT | TGCCTCCAGG | TCCCAGTGAA | TGAAAACGAC | 540 |
| ATGAAGGTAG | ATGAAGTCCT | TTACGAAGAC | TCGTCAACAG | CTTAAATCTG | GATTACTACA | 600 |
| GCCAAATAAT | CAGTGTTTTA | TATGAGAGTA | AAGCAAAGTA | TGTGTATTTT | TCCCTTGTCA | 660 |
| AAAATTAGTT | GAAATTGTTC | ATTAATGTGA | ATACAGACTG | CATTTTAAAA | TTGTAATTAT | 720 |
| GAAATACCTT | ATATAAAACC | ATCTTTAAAA | ACCAATAGAA | GTGTGAATAG | TAGAATATTA | 780 |
| ATTAAAATGG | AGGCTATCAG | CCTGTGATTT | TCAGCTTAAA | AAAAAAAAAA | AA | 832 |

( 2 ) INFORMATION FOR SEQ ID NO:12:

( i ) SEQUENCE CHARACTERISTICS:
        ( A ) LENGTH: 856 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:12:

| | | | | | |
|---|---|---|---|---|---|
| GTGAGCAGCG | CCAAGCGGAG | CTGCGGGGAG | AGCTGAAGCA | GCGTCTGCGG | GCGATGAGTG | 60 |
| CCGAGGAGCG | TACGCCAGTC | CCTCGTACTG | AGCCAGAAGG | TGCGAGGCCG | CCCGTAGCGG | 120 |
| AAGCCGCGGC | GGACAGACCC | TCCGAAGCTG | GCGGCCAGCG | ATTGCTGATC | TGTGCATGGT | 180 |
| GATTGCCCAC | AGTGAGTATC | AAAAGTCCAA | AAGAATTTCC | ATCTTTCTGA | GCATGCAAGA | 240 |
| TGAAATTGAG | ACAGAAGAGA | TCATCAAGGA | CATTTTCCAA | CGAGGCAAAA | TCTGCTTCAT | 300 |
| CCCTCGGTAC | CCGTTCCAGA | GCAATCACAT | GGATATGGTG | AGAATAGAAT | CACCAGAGGA | 360 |
| AATTTCTTTA | CTTCCCAAAA | CATCCTGGAA | TATCCCTCAG | CCTGGTGAGG | GTGATGTTCG | 420 |
| GGAGGAGGCC | TTGTCCACAG | GGGGACTTGA | TCTCATCTTC | ATGCCAGGCC | TTGGGTTTGA | 480 |
| CAAACATGGC | AACCGACTGG | GGAGGGGCAA | GGGCTACTAT | GATGCCTATC | TGAAGCGCTG | 540 |
| TTTGCAGCAT | CAGGAAGTGA | AGCCCTACAC | CCTGGCGTTG | GCTTTCAAAG | AACAGATTTG | 600 |
| CCTCCAGGTC | CCAGTGAATG | AAAACGACAT | GAAGGTAGAT | GAAGTCCTTT | ACGAAGACTC | 660 |
| GTCAACAGCT | TAAATCTGGA | TTACTACAGC | CAAATAATCA | GTGTTTTATA | TGAGACTAAA | 720 |
| GCAAAGTATG | TGTATTTTC | CCTTGTCAAA | AATTAGTTGA | AATTGTTCAT | TAATGTGAAT | 780 |
| ACAGACTGCA | TTTTAAAATT | GTAATTATGA | AATACCTTAT | ATAAACCAT | CTTTAAAAAC | 840 |
| CAAAAAAAAA | AAAAA | | | | | 856 |

( 2 ) INFORMATION FOR SEQ ID NO:13:

( i ) SEQUENCE CHARACTERISTICS:
        ( A ) LENGTH: 867 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:13:

| | | | | | |
|---|---|---|---|---|---|
| GCGACACTTA | TAAAATAACT | TGCATCTAGG | CTGGGCGTGG | CGGCTCACGC | TGTAATCCCA | 60
| GCACTTTGGG | AGGCCGAAGT | GGGTGGATCA | CTTGAGGCCA | GGAGTTTGAG | ACCAGCCTGG | 120
| CCAACATGGT | GAAACCCCAT | CTCTATCAGA | AATACAAAAG | AATTTCCATC | TTTCTGAGCA | 180
| TGCAAGATGA | AATTGAGACA | GAAGAGATCA | TCAAGGACAT | TTTCCAACGA | GGCAAAATCT | 240
| GCTTCATCCC | TCGGTACCGG | TTCCAGAGCA | ATCACATGGA | TATGGTGAGA | ATAGAATCAC | 300
| CAGAGGAAAT | TTCTTTACTT | CCCAAAACAT | CCTGGAATAT | CCCTCAGCCT | GGTGAGGGTC | 360
| ATGTTCGGGA | GGAGGCCTTG | TCCACAGGGG | GACTTGATCT | CATCTTCATG | CCAGGCCTTG | 420
| GGTTGACAA | ACATGGCAAC | CGACTGGGGA | GGGGCAAGGG | CTACTATGAT | GCCTATCTGA | 480
| AGCGCTGTTT | GCAGCATCAG | GAAGTGAAGC | CCTACACCCT | GGCGTTGGCT | TTCAAAGAAC | 540
| AGATTTGCCT | CCAGGTCCCA | GTGAATGAAA | ACGACATGAA | GGTAGATGAA | GTCCTTTACG | 600
| AAGACTCGTC | AACAGCTTAA | ATCTGGATTA | CTACAGCCAA | ATAATCAGTG | TTTTATATGA | 660
| GAGTAAAGCA | AAGTATGTGT | ATTTTTCCCT | TGTCAAAAAT | TAGTTGAAAT | TGTTCATTAA | 720
| TGTGAATACA | GACTGCATTT | TAAAATTCTA | ATTATGAAAT | ACCTTATATA | AAACCATCTT | 780
| TAAAAACCAA | TAGAAGTGTG | AATAGTAGAA | TATTAATTAA | AATGGAGGCT | ATCAGCCTGT | 840
| GATTTTCAGC | TTAAAAAAAA | AAAAAAA | | | | 867

( 2 ) INFORMATION FOR SEQ ID NO:14:

( i ) SEQUENCE CHARACTERISTICS:
        ( A ) LENGTH: 1220 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:14:

| | | | | | |
|---|---|---|---|---|---|
| CGGTGGGAGC | CAAGATACAG | AGGTAAAATA | AAGCATACTC | TAGGAAAAGC | ATGTGAAATG | 60
| ACCGAAGACT | ACTAAAATGG | ATAGGTGGGG | ATCAAGCCTG | GAATTCTCTG | GATAGACAGC | 120
| TTGTCTCCAC | AGTGACCTTT | TAATGAGTTT | TCACACCTAC | CAGAGTGGGT | GTACCAGGAA | 180
| GGGATAAAAG | GAGCAGGTAA | GTGCTGGGTC | CCAAACTAAA | AGTCAGGCTT | CATGATGCAA | 240
| CACTGTCTGA | CCCACTATAT | CACTCTGGTC | CCCCCCCTTT | TTTTTCTTT | TAAATATTTA | 300
| AAGAAATTGG | AGAAGGCTGA | GAGAGAAGGA | GGAATTGTTA | AGAGGAGTTG | CTAAATATAG | 360
| TCTTGGAAAA | TATAATTGCC | ATAATTTCCC | ATTTAGGTGA | TTGCCCACAG | TGAGTATCAA | 420
| AAGTCCAAAA | GAATTTCCAT | CTTTCTGAGC | ATGCAAGATG | AAATTGAGAC | AGAAGAGATC | 480
| ATCAAGGACA | TTTTCCAACG | AGGCAAAATC | TGCTTCATCC | CTCGGTACCG | GTTCCAGAGC | 540
| AATCACATGG | ATATGGTGAG | AATAGAATCA | CCAGAGGAAA | TTTCTTTACT | TCCCAAAACA | 600
| TCCTGGAATA | TCCCTCAGCC | TGGTGAGGGT | GATGTTCGGG | AGGAGGCCTT | GTCCACAGGT | 660
| ATAGAAGACA | GAACTGAACT | TCAAGCCTGA | TGGTGCTCTG | GCAACAGAAA | GAGGACACGA | 720
| GGGAGTAAAG | TCCAAATTCA | CAGTCCACTG | TCAATCCCAA | GAGGGACAAA | TGAGCTGGAC | 780
| AGGAACAGGG | AGGAAAGACA | GAGGGGGACT | TGATCTCATC | TTCATGCCAG | GCCTTGGGTT | 840
| TGACAAACAT | GGCAACCGAC | TGGGGAGGGG | CAAGGGCTAC | TATGATGCCT | ATCTGAAGCG | 900
| CTGTTTGCAG | CATCAGGAAG | TGAAGCCCTA | CACCCTGGCG | TTGGCTTTCA | AGAACAGAT | 960

| | | | | | |
|---|---|---|---|---|---|
| TTGCCTCCAG | GTCCCAGTGA | ATGAAAACGA | CATGAAGGTA | GATGAAGTCC | TTTACGAAGA | 1020
| CTCGTCAACA | GCTTAAATCT | GGATTACTAC | AGCCAAATAA | TCAGTGTTTT | ATATGAGAGT | 1080
| AAAGCAAAGT | ATGTGTATTT | TTCCCTTGTC | AAAAATTAGT | TGAAATTGTT | CATTAATGTG | 1140
| AATACAGACT | GCATTTTAAA | ATTGTAATTA | TGAAATACCT | TATATAAAAC | CATCTTTAAA | 1200
| AACCAAAAAA | AAAAAAAAA  | | | | | 1220

CDNA PROBES AND ANTIBODIES FOR HUMAN METHENYLTETRAHYDROFOLATE SYNTHETASE

This is a continuation-in-part of U.S. application Ser. No. 08/033,857 filed on Mar. 19, 1993, now U.S. Pat. No. 5,389,516.

BACKGROUND OF THE INVENTION (a) Field of the Invention

The invention relates to cDNA probes and antibodies for the detection of human methenyltetrahydrofolate synthetase (MTHFS) in biological tissue samples to determine the appropriate chemotherapy for a given patient treated with the reduced folate Leucovorin™.

(b) Description of Prior Art

Many plant and animal tissues contain folic acid (pteroylglutamic acid) as the polyglutamates of the reduced tetrahydro forms. These folates act as co-enzymes for processes in which there is transfer of a one-carbon unit (e.g., in purine and pyrimidine nucleotide biosynthesis), amino acid conversions (e.g., histidine to glutamic acid through forminoglutamic acid), and generation and use of formate.

Absorption of folic acid takes place in the small intestine. In the epithelial cells, folic acid are reduced to dihydro- and tetrahydrofolates. They are bound to protein and transported as methyl tetrahydrofolate. Serum levels vary from 3 to 21 ng/mL and closely reflect dietary intake. Red blood cell (RBC) folate, normal 160 to 640 ng/ml whole blood (corrected to packed cell volume of 45%), is a better indicator of the folate status. The total body folate is about 70 mg, ⅓ of which is found in the liver. About 20% of ingested folate is excreted unabsorbed together with 60 to 90 μg/day of ingested folate not reabsorbed from bile. Reduced folates are present in all living tissues although decreased amounts of certain reduced folates in cancer cells are thought to be responsible for the inefficacy of the anti-cancer agent 5-fluorouracil (Ullman, B. et al., *Proc. Natl. Acad. Sci. USA*, 75:980–983, 1978). 5-formyltetrahydrofolate is thus administered clinically, as Leucovorin™, in association with 5-fluorouracil to enhance its cytotoxic effects through amplification of intracellular reduced folate pools (Grem JL et al., *Cancer Treat. Rep.*, 71:1249–64, 1987).

Methenyltetrahydrofolate synthetase (MTHFS; 5-formyltetrahydrofolate cyclodehydrase, EC 6.3.3.2), a 27 KDa monomer, catalyzes the unidirectional transformation of 5-formyltetrahydrofolate to 5-10-methenyltetrahydrofolate and requires ATP and divalent cations. MTHFS activity has been purified from sheep liver, *Lactobacillus casei*, rabbit and human liver (Bertrand R. et al., *Bioch. Biophys. Acta*, 911:154–61, 1987).

MTHFS is the obligatory initial metabolic step prior to 5-formyltetrahydrofolate's intracellular conversion to other reduced folates and one experimental model suggests that variations in MTHFS activity between different tissues can influence intracellular 5-formyltetrahydrofolate interconversion to other reduced folates and its ability to enhance 5-fluorouracil activity (Mullin R. J. et al., "The expanding role of folates and fluoropyrimidines in Cancer Chemotherapy", Plenum, New York, pp. 25–38, 1988). The enzyme might thus play a role in the cellular pharmacology of Leucovorin™.

Physiologically, 5-formyltetrahydrofolate is produced through hydrolysis of 5-10-methenyltetrahydrofolate by a serine hydroxymethyltransferase-glycine complex (Stover P. et al., *J. Biol. Chem.*, 265:14227–14233, 1990). The 5-formyltetrahydrofolate polyglutamates thus formed can then directly inhibit serine hydroxymethyltransferase, the main source of one carbon residues for folate-dependent syntheses (Stover P. et al., *J. Biol. Chem.*, 266:1543–1550, 1991).

Inhibitory studies have demonstrated that MTHFS prevents 5-formyltetrahydrofolate polyglutamates from accumulating intracellularly and inhibiting de novo purine synthesis (Bertrand R. et al., *J. Biol. Chem.*, 264:8843–6, 1989). MTHFS might thus also play an important physiological function in eliminating inhibitory 5-formyltetrahydrofolate polyglutamates.

A cDNA for human methenyltetrahydrofolate synthetase (MTHFS) has been isolated from a human liver cDNA library and sequenced. The nucleotide and derived amino acid sequences are unique and share a 28% amino acid homology with an *E. coli* protein of unknown function. The identity of the cDNA was confirmed by immunizing rabbits with a 12 amino acid peptide chosen from the derived amino acid sequence and obtaining antibodies immunoblotting against human MTHFS.

There is a test, called "CEA test", for the determination of carcinoembryonic antigen (CEA) in the serum of a patient. CEA is present in the serum of 70% of patients with colo-rectal adenocarcinoma. However, the "CEA test" does not allow for the prognosis of a treatment of a patient with an anti-tumor agent.

It would be highly desirable to be provided with a test which would allow to predict the efficacy of Leucovorin-containing chemotherapy regimens in patients with colo-rectal malignancies.

SUMMARY OF THE INVENTION

One aim of the present invention is to provide for a prognostic test which would allow for the choice of an appropriate chemotherapy treatment for a given patient with colo-rectal carcinoma.

Another aim of the present invention is to provide for cDNA and antibodies to assay MTHFS in human colo-rectal tumors. A low enzyme expression would predict poor efficacy for Leucovorin™-containing regimens and alert physicians not to administer potentially inefficient therapy.

Surprisingly and in accordance with the present invention there is provided a cDNA probe for the detection of human methenyltetrahydrofolate synthetase mRNA which comprises the following nucleic acid sequence, Seq. Id. No. 1:

|     |     |     |     |     |     |     |     |     |     |     | G   | GCC | AAC | −1 |
|-----|-----|-----|-----|-----|-----|-----|-----|-----|-----|-----|-----|-----|-----|----|
| ATG | GTG | AAA | CCC | CAT | CTC | TAT | CAG | AAA | TAC | AAA | AGA | ATT | TCC | ATC | 45 |
| TTT | CTG | AGC | ATG | CAA | GAT | GAA | ATT | GAG | ACA | GAA | GAG | ATC | ATC | AAG | 90 |

-continued

| | | | | | | | | | | | | | | |
|---|---|---|---|---|---|---|---|---|---|---|---|---|---|---|
| GAC | ATT | TTC | CAA | CGA | GGC | AAA | ATC | TGC | TTC | ATC | CCT | CGG | TAC | CGG | 135 |
| TTC | CAG | AGC | AAT | CAC | ATG | GAT | ATG | GTG | AGA | ATA | GAA | TCA | CCA | GAG | 180 |
| GAA | ATT | TCT | TTA | CTT | CCC | AAA | ACA | TCC | TGG | AAT | ATC | CCT | CAG | CCT | 225 |
| GGT | GAG | GGT | GAT | GTT | CGG | GAG | GAG | GCC | TTG | TCC | ACA | GGG | GGA | CTT | 270 |
| GAT | CTC | ATC | TTC | ATG | CCA | GGC | CTT | GGG | TTT | GAC | AAA | CAT | GGC | AAC | 315 |
| CGA | CTG | GGG | AGG | GGC | AAG | GGC | TAC | TAT | GAT | GCC | TAT | CTG | AAG | CGC | 360 |
| TGT | TTG | CAG | CAT | CAG | GAA | GTG | AAG | CCC | TAC | ACC | CTG | GCG | TTG | GCT | 405 |
| TTC | AAA | GAA | CAG | ATT | TGC | CTC | CAG | GTC | CCA | GTG | AAT | GAA | AAC | GAC | 450 |
| ATG | AAG | GTA | GAT | GAA | GTC | CCT | T | | | | | | | | 472 | or any functional analogs thereof wherein the hybridization of the probe and the mRNA for human methenyltetrahydrofolate synthetase is substantially preserved. In addition to the sequence above, the DNA sequence of specific clones of MTHFS are disclosed in Tables 1–5.

Surprisingly and in accordance with the present invention, there is also provided an anti-MT-HFS antibody or antigen-binding fragment thereof raised against a protein segment aa$^{100-112}$ (H-Phe-Asp-Lys-His-Gly-Asn-Arg-Leu-Gly-Arg-Gly-Lys-OH or H-FDKHGNRLGRGK-OH, Seq. Id. No. 2) of methenyltetrahydrofolate synthetase human MTHFS to assay MTHFS in a biological tissue sample.

There is also provided in accordance with the present invention, a Western blot method for determining the amount of MTHFS in a biological tissue sample, which comprises subjecting the biological tissue sample to an electrophoresis; incubating the electrophoresed biological sample with an anti-MTHFS antibody or antigen-binding fragment thereof specific to MTHFS, whereby the amount of MTHFS present in a biological tissue sample is determined by a Western blot analysis.

BRIEF DESCRIPTION OF THE DRAWINGS

FIG. 1 is a partial restriction map of human methenyltetrahydrofolate synthetase cDNA;

FIG. 2 is the nucleotide and amino acid sequences of human methenyltetrahydrofolate synthetase cDNA, Seq. Id. No. 9;

FIG. 3 is an alignment of the amino acid sequence of human methenyltetrahydrofolate synthetase cDNA Seq. Id. No. 8 with those of an E. coli protein of unknown function, Seq. Id. No. 7;

FIGS. 6A, 6B, 6C, and 6D collectively depict and compare the nucleotide sequence of human methenyltetrahydrofolate synthetase cDNA clones, MTHFS-1, MTHFS-2, MTHFS-3, MTHFS-4 and MTHFS-5.

DETAILED DESCRIPTION OF THE INVENTION

Figure 4:
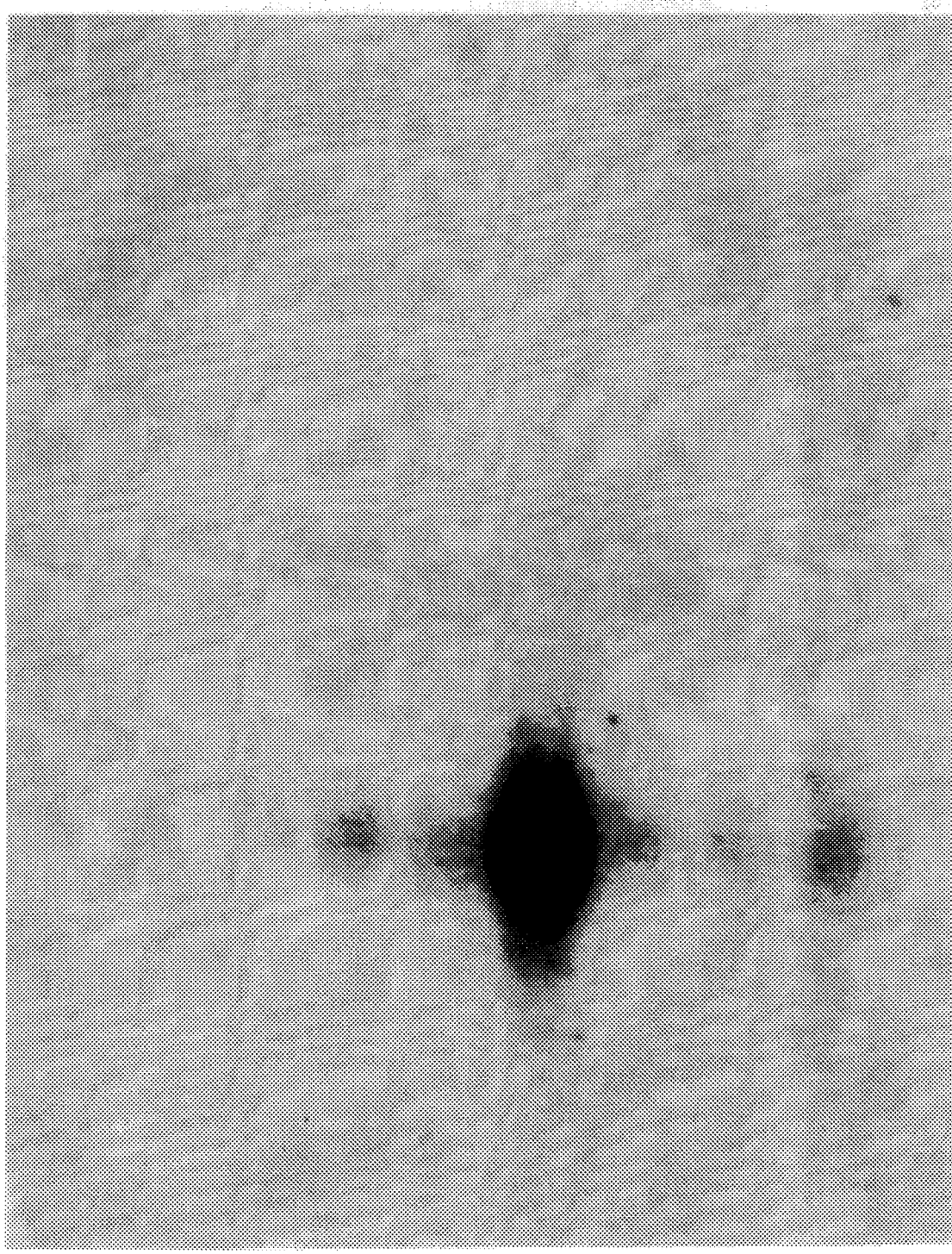
FIG. 4 is a Northern blot of polyA RNA from normal human tissue using $^{32}$p-labeled 238 bp restriction fragment (Sph I/Sty I) of human methenyltetrahydrofolate synthetase cDNA as a probe.

Protein purification and amino acid sequencing.

Human liver MTHFS was purified to homogeneity as previously described by Bertrand R. et al. (Bioch. Biophys. Acta, 91:154–61, 1987). Purified enzyme was chemically cleaved with cyanogen bromide (CnBr) for 22 hours in 70% formic acid under an argon atmosphere and enzymatically digested by protease V8 for 15 hours in 20 mM Tris-HCl (pH 7.5). Following SDS-polyacrylamide electrophoresis in 18% vertical slab gels, fragments were transferred on polyvinylidene difluoride(PVDF) membrane prior to sequencing by automated Edman degradation performed on a model 470A™ Gas-phase sequencer equipped with an on-line model 120A™ phenyl-thiohydantoin analyzer (Applied Biosystem Inc.) employing the general protocol of Hewick et al. (Hewick R. M. et al., *J. Biol. Chem.*, 256:7990–7997, 1981).

Molecular cloning.

The first strand cDNA for polymerase chain reaction (PCR) was synthesized from human liver poly(A)+RNA using Moloney™ murine leukemia virus reverse transcriptase (Stratagene, LaJolla Calif.). The 50 ul reaction contained 1 ug of poly(A)+RNA, 10 pmol of hybrid oligo dT$_{17}$-adapter primer (5'-CCCTCGAGGTCGACGGTATCGT$_{17}$-3', Seq. Id. No. 3), 25 units of enzyme and 250 uM of each dNTPs. Following incubation at 37° C. for 1 hour, an aliquot of the reaction mixture was amplified in 100 ul containing 50 mM KCl, 10 mM Tris-HCl (pH 8.3), 1.5 mM MgCl$_2$, 200 uM dNTPs, 10 units of Taq I™ polymerase (Bethesda Research Laboratories), 10 pmoles of the adapter primer and 300 pmoles of degenerated oligo-nucleotides corresponding to a sequenced heptapeptide obtained from a CnBr fragment. The PCR product of 389 bp was then subcloned into Bluescript™ SK+vector (Stratagene) for sequence analysis and was found to contain nucleotides corresponding to the primer sequence and to an open reading frame of 97 amino acids. This clone was then used as a probe to screen a λDR2 human liver cDNA library (Clontech, Palo Alto, Calif.) at high stringency. Three hundred thousand plaques were screened and positive clones were detected, plaque-purified, subcloned into pGEM and sequenced (Sequenase System, U.S. Biochemical Corp.).

In the Examples below, specific DNA clones of human methenyltetrahydrofolate synthetase are disclosed. Clones MTHFS-1 to MTHFS-5 are disclosed in Tables 1–5. The sequences are shown in their 5' to 3' orientation. Those skilled in the art would make numerous uses of the information. The 5' primers can be derived from these nucleotide sequences and used in Polymerase Chain Reaction for detecting MTHFS in biological tissue samples. Oligonucleotoide probes homologous to the sequence shown in Tables 1–5 can be generated and DNA sequence isolated which hybridizes to the probes. In view of the degeneracy of the genetic code (more than one codon codes for the same amino acid), they can produce different DNA sequence which can code an expression for the same polypeptides coded for an expression by any of the foregoing DNA sequences.

Protein sequencing and cDNA cloning.

A sequence of only six amino acids, Pro-Gly-Leu-Gly-Phe-Asp or PGLGFD, Seq. Id. No. 4, could be firmly established from one of the CnBr fragments due to the small amounts of the purified protein left after purification and was used for MTHFS cDNA cloning. A stretch of 10 amino acids, Gln-Ile-Cys-Leu-Gln-Val-Pro-Val-Asn-Glu or QICLQVPVNE, Seq. Id. No. 5, previously sequenced from a protease V8 digest had not been used to clone the MTHFS cDNA because the sequencing signals, while clearly readable, were judged to be too low to be certain of their accuracy. Degenerate oligonucleotides corresponding to an heptapeptide (Met was assumed to precede the sequenced hexapeptide) were used to amplify a 389 bp cDNA using a 3-' Arg-Ala-Cys-Glu (RACE), Seq. Id. No. 6, PCR protocol (Frohman MA. et al., *Proc. Natl. Acad. Sci. USA*, 85:8998, 1988). This PCR product was subcloned for sequencing analysis and found to contain nucleotides corresponding to the primer sequence and to an open reading frame of 97 amino acids. This PCR pproduct was then used as a probe to screen λDR2 human liver cDNA library (Clontech) and a clone of 867 bp was obtained and contains a Met initiation translation codon preceded by a consensus Kosac motif (FIG. 1). The 5-' and 3-' untranslated regions are 125 and 247 bp respectively. The open reading frame corresponds to a sequence of 164 amino acids. The resulting protein contains the two sequenced peptides obtained from purified MTHFS protein (I and II, FIG. 1), an ATP consensus binding site (III, FIG. 1) and 4 consensus putative phosphorylation sites (IV, FIG. 1).

The human liver MTHFS nucleic acid sequence with the coding region indicated by its amino acid sequence underneath is illustrated in FIG. 2.

The sequence from the 867 bp clone was used to search the Gen Bank™/EMBL Data Bank. This revealed a 28% amino acid homology with a bacterial protein of unknown function (FIG. 3) (Hsu, LM. et al., *J. Bacteriology*, 161:1162–1170, 1985). The sequence of this *E. coli* protein was deduced from a 540 nucleotide sequence open reading frame (ORF) placed immediately after a 6S RNA gene and encodes for a 21 kD protein. There is also a 92% homology between nucleotides 30 to 160 in the 5' non-coding region and the first monomer of Alu type sequences.

In accordance with the present invention, both cDNA probes and antibodies for the detection of MTHFS may be used to determine the level in a given biological sample of MTHFS which is associated with human tumors. Low enzyme expression would predict poor efficacy for Leucovorin™-containing regimens and alert physicians not to administer potentially inefficient therapy.

Biological tissue samples in accordance with the present invention may be neoplastic tissues, such as human colorectal tumor extracts or extracts from any other malignant tissues, and corresponding normal tissues of a given patient.

The level of the MTHFS enzyme in a biological sample may be measured in Mol/mg tissue.

A low level of the MTHFS enzyme in a given neoplastic tissue sample may be determined by comparison to the level of MTHFS in the normal tissue of the patient.

EXAMPLE I cDNA probe useful for the detection of Human MTHFS mRNA cDNA probes for the detection of the mRNA of human methenyltetrahydrofolate synthetase (MTHFS) are obtained by using a restriction fragment (EaeI/HincII) as a probe. The resulting probe has the following nucleic acid (−7–472 bp of MTHFS) sequence, Seq. Id. No. 1:

```
                                                    G   GCC AAC  -1
ATG GTG AAA CCC CAT CTC TAT CAG AAA TAC AAA AGA ATT TCC ATC  45
TTT CTG AGC ATG CAA GAT GAA ATT GAG ACA GAA GAG ATC ATC AAG  90
GAC ATT TTC CAA CGA GGC AAA ATC TGC TTC ATC CCT CGG TAC CGG 135
ATC CAG AGC AAT CAC ATG GAT ATG GTG AGA ATA GAA TCA CCA GAG 180
GAA ATT TCT TTA CTT CCC AAA ACA TCC TGG AAT ATC CCT CAG CCT 225
GGT GAG GGT GAT GTT CGG GAG GAG GCC TTG TCC ACA GGG GGA CTT 270
GAT CTC ATC TTC ATG CCA GGC CTT GGG TTT GAC AAA CAT GGC AAC 315
CGA CTG GGG AGG GGC AAG GGC TAC TAT GAT GCC TAT CTG AAG CGC 360
TGT TTG CAG CAT CAG GAA GTG AAG CCC TAC ACC CTG GCG TTG GCT 405
```

-continued

| TTC | AAA | GAA | CAG | ATT | TGC | CTC | CAG | GTC | CCA | GTG | AAT | GAA | AAC | GAC | 450 |
| ATG | AAG | GTA | GAT | GAA | GTC | CCT | T | | | | | | | | 472 |

TABLE 1

DNA sequence of clone MTHFS-1

| GCGTGGGCGT | GAGATGGCGG | CGGCAGCGGT | GAGCAGCGCC | AAGCGGAGCC | 50 |
| TGCGGGGAGA | GCTGAAGCAG | CGTCTGCGGG | CGATGAGTGC | CGAGGAGCGG | 100 |
| CTACGCCAGT | CCCGCGTACT | GACCCAGAAG | GTGATTGCCC | ACAGTGAGTA | 150 |
| TCAAAAGTCC | AAAAGAATTT | CCATCTTTCT | GAGCATGCAA | GATGAAATTG | 200 |
| AGACAGAAGA | GATCATCAAG | GACATTTTCC | AACGAGGCAA | AATCTGCTTC | 250 |
| ATCCCTCGGT | ACCGGTTCCA | GAGCAATCAC | ATGGATATGG | TGAGAATAGA | 300 |
| ATCACCAGAG | GAAATTTCTT | TACTTCCCAA | ACATCCTGG | AATATCCCTC | 350 |
| AGCCTGGTGA | GGGTGATGTT | CGGGAGGAGG | CCTTGTCCAC | AGGGGGACTT | 400 |
| GATCTCATCT | TCATGCCAGG | CCTTGGGTTT | GACAAACATG | GCAACCGACT | 450 |
| GGGGAGGGGC | AAGGGCTACT | ATGATGCCTA | TCTGAAGCGC | TGTTTGCAGC | 500 |
| ATCAGGAAGT | GAAGCCCTAC | ACCCTGGCGT | TGGCTTTCAA | AGAACAGATT | 550 |
| TGCCTCCAGG | TCCCAGTGAA | TGAAAACGAC | ATGAAGGTAG | ATGAAGTCCT | 600 |
| TTACGAAGAC | TCGTCAACAG | CTTAAATCTG | GATTACTACA | GCCAAATAAT | 650 |
| CAGTGTTTTA | TATGAGAGTA | AAGCAAAGTA | TGTGTATTTT | TCCCTTGTCA | 700 |
| AAAATTAGTT | GAAATTGTTC | ATTAATGTGA | ATACAGACTG | CATTTTAAAA | 750 |
| TTGTAATTAT | GAAATACCTT | ATATAAAACC | ATCTTTAAAA | ACCAATAGAA | 800 |
| GTGTGAATAG | TAGAATATTA | ATTAAAATGG | AGGCTATCAG | CCTGTGATTT | 850 |
| TCAGCTTAAA | AAAAAAAAAA | AA | | | 872 |

TABLE 2

DNA sequence of clone MTHFS-2

| GGCACGAGCG | AGAGCGAGAG | GGCCGCGGGC | GGCGGAGGCA | GCGGGGCCGG | 50 |
| GATGGAGGAC | GTTAACTCTA | ACGTGAACGC | GGACCAGGAG | GTGATTGCCC | 100 |

TABLE 2-continued

DNA sequence of clone MTHFS-2

| | | | | | |
|---|---|---|---|---|---|
| ACAGTGAGTA | TCAAAAGTCC | AAAAGAATTT | CCATCTTTCT | GAGCATGCAA | 150 |
| GATGAAATTG | AGACAGAAGA | GATCATCAAG | GACATTTTCC | AACGAGGCAA | 200 |
| AATCTGCTTC | ATCCCTCGGT | ACCGGTTCCA | GAGCAATCAC | ATGGATATGG | 250 |
| TGAGAATAGA | ATCACCAGAG | GAAATTTCTT | TACTTCCCAA | AACATCCTGG | 300 |
| AATATCCCTC | AGCCTGGTGA | GGGTGATGTT | CGGGAGGAGG | CCTTGTCCAC | 350 |
| AGGGGACTT | GATCTCATCT | TCATGCCAGG | CCTTGGGTTT | GACAAACATG | 400 |
| GCAACCGACT | GGGGAGGGGC | AAGGGCTACT | ATGATGCCTA | TCTGAAGCCC | 450 |
| TGTTTGCAGC | ATCAGGAAGT | GAAGCCCTAC | ACCCTGGCGT | TGGCTTTCAA | 500 |
| AGAACAGATT | TGCCTCCAGG | TCCCAGTGAA | TGAAAACGAC | ATGAAGGTAG | 550 |
| ATGAAGTCCT | TTACGAAGAC | TCGTCAACAG | CTTAAATCTG | GATTACTACA | 600 |
| GCCAAATAAT | CAGTGTTTTA | TATGAGAGTA | AAGCAAAGTA | TGTGTATTTT | 650 |
| TCCCTTGTCA | AAAATTAGTT | GAAATTGTTC | ATTAATGTGA | ATACAGACTG | 700 |
| CATTTAAAA | TTGTAATTAT | GAAATACCTT | ATATAAAACC | ATCTTTAAAA | 750 |
| ACCAATAGAA | GTGTGAATAG | TAGAATATTA | ATTAAAATGG | AGGCTATCAG | 800 |
| CCTGTGATTT | TCAGCTTAAA | AAAAAAAAA | AA | | 832 |

TABLE 3

DNA sequence of clone MTHFS-3

| | | | | | |
|---|---|---|---|---|---|
| GTGAGCAGCG | CCAAGCGGAG | CTGCGGGGAG | AGCTGAAGCA | GCGTCTGCGG | 50 |
| GCGATGAGTG | CCGAGGAGCG | TACGCCAGTC | CCTCGTACTG | AGCCAGAAGG | 100 |
| TGCGAGGCCG | CCCGTAGCGG | AAGCCGCGGC | GGACAGACCC | TCCGAAGCTG | 150 |
| GCGGCCAGCG | ATTGCTGATC | TGTGCATGGT | GATTGCCCAC | AGTGAGTATC | 200 |
| AAAAGTCCAA | AAGAATTTCC | ATCTTTCTGA | GCATGCAAGA | TGAAATTGAG | 250 |
| ACAGAAGAGA | TCATCAAGGA | CATTTTCCAA | CGAGGCAAAA | TCTGCTTCAT | 300 |
| CCCTCGGTAC | CCGTTCCAGA | GCAATCACAT | GGATATGGTG | AGAATAGAAT | 350 |
| CACCAGAGGA | AATTTCTTTA | CTTCCCAAAA | CATCCTGGAA | TATCCCTCAG | 400 |
| CCTGGTGAGG | GTGATGTTCG | GGAGGAGGCC | TTGTCCACAG | GGGACTTGA | 450 |

TABLE 3-continued

DNA sequence of clone MTHFS-3

| | | | | |
|---|---|---|---|---|
| TCTCATCTTC | ATGCCAGGCC | TTGGGTTTGA | CAAACATGGC | AACCGACTGG 500 |
| GGAGGGGCAA | GGGCTACTAT | GATGCCTATC | TGAAGCGCTG | TTTGCAGCAT 550 |
| CAGGAAGTGA | AGCCCTACAC | CCTGGCGTTG | GCTTTCAAAG | AACAGATTTG 600 |
| CCTCCAGGTC | CCAGTGAATG | AAAACGACAT | GAAGGTAGAT | GAAGTCCTTT 650 |
| ACGAAGACTC | GTCAACAGCT | TAAATCTGGA | TTACTACAGC | CAAATAATCA 700 |
| GTGTTTTATA | TGAGACTAAA | GCAAAGTATG | TGTATTTTTC | CCTTGTCAAA 750 |
| AATTAGTTGA | AATTGTTCAT | TAATGTGAAT | ACAGACTGCA | TTTTAAAATT 800 |
| GTAATTATGA | AATACCTTAT | ATAAAACCAT | CTTTAAAAAC | CAAAAAAAAA 850 |
| AAAAA | | | | 856 |

TABLE 4

DNA sequence of clone MTHFS-4

| | | | | |
|---|---|---|---|---|
| GCGACACTTA | TAAAATAACT | TGCATCTAGG | CTGGGCGTGG | CGGCTCACGC 50 |
| TGTAATCCCA | GCACTTTGGG | AGGCCGAAGT | GGGTGGATCA | CTTGAGGCCA 100 |
| GGAGTTTGAG | ACCAGCCTGG | CCAACATGGT | GAAACCCCAT | CTCTATCAGA 150 |
| AATACAAAAG | AATTTCCATC | TTTCTGAGCA | TGCAAGATGA | AATTGAGACA 200 |
| GAAGAGATCA | TCAAGGACAT | TTTCCAACGA | GGCAAAATCT | GCTTCATCCC 250 |
| TCGGTACCGG | TTCCAGAGCA | ATCACATGGA | TATGGTGAGA | ATAGAATCAC 300 |
| CAGAGGAAAT | TTCTTTACTT | CCCAAAACAT | CCTGGAATAT | CCCTCAGCCT 350 |
| GGTGAGGGTC | ATGTTCGGGA | GGAGGCCTTG | TCCACAGGGG | GACTTGATCT 400 |
| CATCTTCATG | CCAGGCCTTG | GGTTTGACAA | ACATGGCAAC | CGACTGGGGA 450 |
| GGGGCAAGGG | CTACTATGAT | GCCTATCTGA | AGCGCTGTTT | GCAGCATCAG 500 |
| GAAGTGAAGC | CCTACACCCT | GGCGTTGGCT | TTCAAAGAAC | AGATTTGCCT 550 |
| CCAGGTCCCA | GTGAATGAAA | ACGACATGAA | GGTAGATGAA | GTCCTTTACG 600 |
| AAGACTCGTC | AACAGCTTAA | ATCTGGATTA | CTACAGCCAA | ATAATCAGTG 650 |
| TTTTATATGA | GAGTAAAGCA | AGTATGTGT | ATTTTCCCT | TGTCAAAAAT 700 |

TABLE 4-continued

DNA sequence of clone MTHFS-4

| | | | | |
|---|---|---|---|---|
| TAGTTGAAAT | TGTTCATTAA | TGTGAATACA | GACTGCATTT | TAAAATTCTA 750 |
| ATTATGAAAT | ACCTTATATA | AAACCATCTT | TAAAAACCAA | TAGAAGTGTG 800 |
| AATAGTAGAA | TATTAATTAA | AATGGAGGCT | ATCAGCCTGT | GATTTTCAGC 850 |
| TTAAAAAAAA | AAAAAA | | | 867 |

TABLE 5

DNA sequence of clone MTHFS-5

| | | | | |
|---|---|---|---|---|
| CGGTGGGAGC | CAAGATACAG | AGGTAAAATA | AAGCATACTC | TAGGAAAAGC 50 |
| ATGTGAAATG | ACCGAAGACT | ACTAAAATGG | ATAGGTGGGG | ATCAAGCCTG 100 |
| GAATTCTCTG | GATAGACAGC | TTGTCTCCAC | AGTGACCTTT | TAATGAGTTT 150 |
| TCACACCTAC | CAGAGTGGGT | GTACCAGGAA | GGGATAAAAG | GAGCAGGTAA 200 |
| GTGCTGGGTC | CCAAACTAAA | AGTCAGGCTT | CATGATGCAA | CACTGTCTGA 250 |
| CCCACTATAT | CACTCTGGTC | CCCCCCCTTT | TTTTTCTTT | TAAATATTTA 300 |
| AAGAAATTGG | AGAAGGCTGA | GAGAGAAGGA | GGAATTGTTA | AGAGGAGTTG 350 |
| CTAAATATAG | TCTTGGAAAA | TATAATTGCC | ATAATTTCCC | ATTTAGGTGA 400 |
| TTGCCCACAG | TGAGTATCAA | AAGTCCAAAA | GAATTTCCAT | CTTTCTGAGC 450 |
| ATGCAAGATG | AAATTGAGAC | AGAAGAGATC | ATCAAGGACA | TTTTCCAACG 500 |
| AGGCAAAATC | TGCTTCATCC | CTCGGTACCG | GTTCCAGAGC | AATCACATGG 550 |
| ATATGGTGAG | AATAGAATCA | CCAGAGGAAA | TTTCTTTACT | TCCCAAAACA 600 |
| TCCTGGAATA | TCCCTCAGCC | TGGTGAGGGT | GATGTTCGGG | AGGAGGCCTT 650 |
| GTCCACAGGT | ATAGAAGACA | GAACTGAACT | TCAAGCCTGA | TGGTGCTCTG 700 |
| GCAACAGAAA | GAGGACACGA | GGGAGTAAAG | TCCAAATTCA | CAGTCCACTG 750 |
| TCAATCCCAA | GAGGGACAAA | TGAGCTGGAC | AGGAACAGGG | AGGAAAGACA 800 |
| GAGGGGGACT | TGATCTCATC | TTCATGCCAG | GCCTTGGGTT | TGACAAACAT 850 |
| GGCAACCGAC | TGGGGAGGGG | CAAGGGCTAC | TATGATGCCT | ATCTGAAGCG 900 |
| CTGTTTGCAG | CATCAGGAAG | TGAAGCCCTA | CACCCTGGCG | TTGGCTTTCA 950 |
| AAGAACAGAT | TTGCCTCCAG | GTCCCAGTGA | ATGAAAACGA | CATGAAGGTA 1000 |
| GATGAAGTCC | TTTACGAAGA | CTCGTCAACA | GCTTAAATCT | GGATTACTAC 1050 |

TABLE 5-continued

DNA sequence of clone MTHFS-5

| | | | | | |
|---|---|---|---|---|---|
| AGCCAAATAA | TCAGTGTTTT | ATATGAGAGT | AAAGCAAAGT | ATGTGTATTT | 1100 |
| TTCCCTTGTC | AAAAATTAGT | TGAAATTGTT | CATTAATGTG | AATACAGACT | 1150 |
| GCATTTTAAA | ATTGTAATTA | TGAAATACCT | TATATAAAAC | CATCTTTAAA | 1200 |
| AACCAAAAAA | AAAAAAAAAA | | | | 1220 |

FIG. 4 shows a Northern blot of polyA RNA from normal human tissues. The hybridization was carried out with 32P-labeled 238 bp restriction fragment (Sph I/Sty I) of human methenyltetrahydrofolate synthetase cDNA as a probe. The human tissues of FIG. 4 are as follows: 2) heart, 3) brain, 4) placenta, 5) lung, 6) liver, 7) skeletal muscle, 8) kidney, and 9) pancreas. The transcript is approximately 0.9 kb in size.

The above-described cDNA may be used to assay the level in a given biological sample of MTHFS which is associated with human tumors. Low enzyme expression would predict poor efficacy for Leucovorin™ containing regimens and alert physicians not to administer potentially inefficient therapy.

EXAMPLE II

Anti-MTHFS Antibody

A peptide representing the protein segment 100-112 (H-Phe-Asp-Lys-His-Gly-Asn-Arg-Leu-Gly-Arg-Gly-Lys-OH or H-FDKHGNRLGRGK-OH, Seq. Id. No. 2) of methenyltetrahydrofolate synthetase was synthesized by a solid-phase technique, using a scheme based on t-Boc chemistry/acid labile amino acid protecting groups. The crude peptide was purified in one step by preparative high pressure liquid chromatography (HPLC) on a Partisil 10 ODS-3 Whatman™ column (10μ particle size; 2.2 cm×50 cm), using a binary solvent system consisting of 0.01% tri-fluoroacetic acid (TFA), pH 2.9 and acetonitrile ($CH_3CN$) -0.01% TFA and an appropriate gradient. Elution of the peptide was monitored at 214 nm. Collected fractions were screened by analytical HPLC using UV detection, pooled accordingly, evaporated in vacuo and lyophilized twice. The purified peptide was analyzed for homogeneity by analytical HPLC on a μBondapak C18™ column (10μ particles; 0.39× 15 cm) using appropriate linear gradients of 0.01% TFA, pH 2.9 and $CH_3CN$-0.01% TFA and 0.01M ammonium acetate, pH 6.9 and $CH_3CN$. Its amino acid composition was assessed by quantitative amino acid analysis after acidic hydrolysis in vacuo (6N HCl, 110° C., 118 hours) and phenylisothiocyanate derivatization. Peptide purity was 99% as assessed by reverse-phase HPLC. Amino acid composition (Asx (2), 1.88; G (3), 2.92; H (1), 1.03; R (2), 2.29; L (1), 0.94; F(1), 0.99; K (2), 1.94) and peptide content (70%) were satisfactory.

The pure peptide was adsorbed onto methylated bovine serum albumin (mBSA) as carrier protein, at a ratio of 5 mg peptide/1 mg mBSA and rabbit immunization was performed.

The identity of the cDNA was confirmed by immunizing rabbits with a 12 amino acid peptide (Phe-Asp-Lys-His-Gly-Asn-Arg-Leu-Gly-Arg-Gly-Lys, Seq. Id. No. 2 or FDKHGNRLGRGK) chosen from the derived amino acid sequence $aa^{100-112}$ of MTHFS.

Antibodies were obtained after the third booster injection which reacted against both the immobilized peptide on nitrocellulose and purified human MTHFS on Western blot. Western blot analysis.

Figure 5:
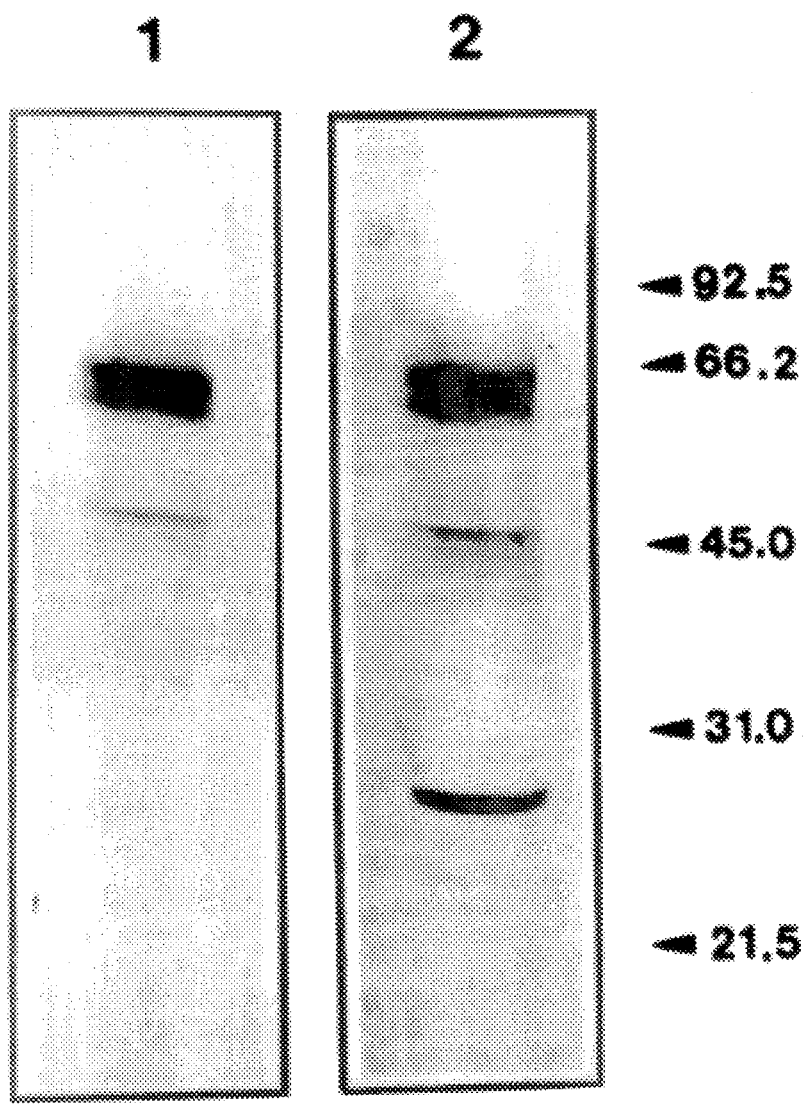
FIG. 5 is a Western blot of pre-immune rabbit serum and polyclonal immune rabbit serum raised against a dodecapeptide (aa$_{100-112}$) of human liver methenyltetrahydrofolate synthetase.

Partially purified MTHFS from human liver was electrophoresed on SDS-polyacrylamide gels (11%), transferred to nitrocellulose and incubated with the obtained rabbit serum after immunization. Human MTHFS proteins were detected with alkaline-phosphatase conjugated antibodies (BRL, Gaithersburg, Md.). The Western blot analysis is shown in FIG. 5 where the arrows and the numbers indicate the migration positions and the size of the Mr markers (kDA).

The antibodies of the present invention may be used to assay the level in a given biological sample of MTHFS which is associated with human tumors. Low enzyme expression would predict poor efficacy for Leucovorin™ containing regimens and alert physicians not to administer potentially inefficient therapy.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A cDNA probe for the detection of a mRNA encoding a for human methenyltetrahydrofolate synthetase (MTHFS), which comprises at least one nucleic acid sequence selected from the group consisting of SEQ ID NO:10, SEQ ID NO:11, SEQ ID NO:12, SEQ ID NO:13, SEQ ID NO:14, and any contiguous sequence of at least twelve nucleotides selected from the MTHFS-encoding region of SEQ ID NO:10, SEQ ID NO: 11, SEQ ID NO:12, SEQ ID NO:13 and SEQ ID NO:14.

2. A Northern blot method for determining the amount of a human MTHFS transcript in a biological tissue sample, which comprises the steps of:

a) labelling a cDNA probe of claim 1;

b) isolating the mRNA present in said biological tissue sample and separating said mRNA on the basis of relative mass by gel electrophoresis;

c) incubating the electrophoresed biological sample of step (b) with the labelled cDNA probe of step (a) whereby the amount of MTHFS transcript present in said biological sample is determined.

3. A diagnostic assay for determining the efficacy of a chemotherapy regimen comprising:

a) collecting biological tissue samples from a patient eligible for 5-formyltetrahydrofolate-containing chemotherapy regimen;

b) determining the representation of human MTHFS mRNA transcript in said the biological tissue samples using the method of claim 2; wherein elevated levels of MTHFS transcript indicates a condition of potentially efficient therapy.

4. A method for detecting the presence of a human MTHFS-encoding target sequence in duplex DNA, comprising:

a) denaturing the duplex DNA;

b) reacting the denatured DNA with a first oligonucleotide probe which is complementary to a first region of the target sequence, and with a second oligonucleotide probe which is complementary to a second region of the target sequence, wherein said first and second target regions are contiguous with one another, under hybridization conditions in which the two probes become stably hybridized to their associated target regions; wherein at least one of said first and second probes is 5' a oligonucleotide primer corresponding to a probe of claim 1;

c) ligating said first and second probes which are hybridized to the target sequence in step (b); and d) testing for the presence of said ligated first and second probes formed in step (c).

* * * * *